United States Patent
Haigh et al.

(10) Patent No.: US 10,891,355 B2
(45) Date of Patent: Jan. 12, 2021

(54) PHARMACY AUTHENTICATION METHODS AND SYSTEMS

(71) Applicant: CVS Pharmacy, Inc., Woonsocket, RI (US)

(72) Inventors: Scott Douglas Haigh, Canton, MA (US); Alfred John Pritchard, II, Highlands, NJ (US); Andrew Jay Schwartz, Waltham, MA (US)

(73) Assignee: CVS Pharmacy, Inc., Woonsocket, RI (US)

( * ) Notice: Subject to any disclaimer, the term of this patent is extended or adjusted under 35 U.S.C. 154(b) by 944 days.

(21) Appl. No.: 14/870,993

(22) Filed: Sep. 30, 2015

(65) Prior Publication Data

US 2017/0091424 A1    Mar. 30, 2017

(51) Int. Cl.
*G06F 19/00*    (2018.01)
*G06Q 50/22*    (2018.01)
*H04L 29/06*    (2006.01)

(52) U.S. Cl.
CPC ......... *G06F 19/3475* (2013.01); *G06Q 50/22* (2013.01); *H04L 63/08* (2013.01)

(58) Field of Classification Search
CPC ............................ G06F 19/3475; G06Q 50/22
See application file for complete search history.

(56) References Cited

U.S. PATENT DOCUMENTS

| | | | |
|---|---|---|---|
| 6,536,659 B1 | 3/2003 | Hauser et al. | |
| 6,854,642 B2 | 2/2005 | Metcalf et al. | |
| 7,478,067 B2 | 1/2009 | Messina | |
| 7,516,886 B2 | 4/2009 | Gangi | |
| 7,983,452 B2 | 7/2011 | Chaney et al. | |
| 8,311,853 B1 * | 11/2012 | Pankow | G06Q 10/00 705/2 |
| 8,380,636 B2 | 2/2013 | Smith, III | |
| 8,626,530 B1 * | 1/2014 | Tran | G06Q 50/22 705/2 |
| 8,694,332 B2 | 4/2014 | Martin et al. | |
| 8,768,838 B1 | 7/2014 | Hoffman | |
| 9,043,012 B2 | 5/2015 | Davey et al. | |

(Continued)

OTHER PUBLICATIONS

Randalls, Pharmacy Prescription Management Application Terms of Use, Oct. 29, 2014, www.randalls.com/terms-of-use/pharmacy-orescription-management-application-terms-of-use.html (Year: 2014).*

(Continued)

*Primary Examiner* — Evangeline Barr
(74) *Attorney, Agent, or Firm* — Patent Law Works LLP (57) ABSTRACT

An electronic image that includes information related to a pharmacy prescription of a user of a first account (e.g., a store account) is received from a client device. The pharmacy prescription information is electronically extracted from the electronic image, and a second account (e.g., a pharmacy account) is identified based thereon. Additional authentication information is received from the client device (sometimes in response to a prompt for additional information based on information contained in the first or second accounts), and the first and second accounts are linked if the additional authentication information is consistent with the user.

20 Claims, 6 Drawing Sheets

(56) References Cited

U.S. PATENT DOCUMENTS

| | | | |
|---|---|---|---|
| 2003/0115142 A1* | 6/2003 | Brickell | G06F 21/31 |
| | | | 705/51 |
| 2006/0064326 A1 | 3/2006 | Tucker | |
| 2008/0222042 A1 | 9/2008 | Moore et al. | |
| 2011/0145147 A1 | 6/2011 | Wylie | |
| 2011/0185406 A1* | 7/2011 | Hirson | G06Q 20/32 |
| | | | 726/6 |
| 2012/0078701 A1* | 3/2012 | Woods | G06Q 20/10 |
| | | | 705/14.25 |
| 2013/0074167 A1* | 3/2013 | Bailey | G06F 21/41 |
| | | | 726/6 |
| 2014/0165171 A1 | 6/2014 | Meng et al. | |
| 2015/0149358 A1* | 5/2015 | Robbin | G06Q 20/40 |
| | | | 705/44 |

OTHER PUBLICATIONS

Center for Democracy & Technology, "Seeing is ID'ing: Facial Recognition & Privacy," CDT comments to the Federal Trade Commission's Dec. 8, 2011 facial recognition forum, Jan. 22, 2012, 17 pgs.

Hayakawa et al., "A smartphone-based medication self-management system with realtime medication monitoring," Applied Clinical Informatics, vol. 4, No. 1, Jan. 30, 2013, pp. 37-52.

\* cited by examiner

| User Number 202 | Username 204 | Password 206 | Challenge Q & A 208 |
|---|---|---|---|
| 1 | example1@email.com | password1 | Q1 & A1 |
| 2 | example2@email.com | password2 | Q2 & A2 |
| 3 | example3@email.com | password3 | Q3 & A3 |
| ... | ... | ... | ... |

| Patient Name 302 | Patient Address 304 | Patient Phone Number 306 | Patient Date of Birth 308 | Prescribing Physician 310 | Insurance Information 312 |
|---|---|---|---|---|---|
| Lastname1, Firstname1 | Address1 | Number1 | DOB1 | Doctor1 | Insurer1 |
| Lastname2, Firstname2 | Address2 | Number2 | DOB2 | Doctor2 | Insurer2 |
| Lastname3, Firstname3 | Address3 | Number3 | DOB3 | Doctor3 | Insurer3 |
| ... | ... | ... | ... | ... | ... |

PHARMACY AUTHENTICATION METHODS AND SYSTEMS

TECHNICAL FIELD

Embodiments of the present invention relate generally to user authentication and, more particularly, to systems and methods for authenticating a user of a first user account to a second user account.

BACKGROUND

When pharmacies fill prescriptions for patients, a pharmacist, technician, or other pharmacy worker typically collects information from the patient—such as, for example, the patient's name, address, date of birth, prescribing physician, and/or insurance information—and stores this information in a pharmacy account in a repository or database. The pharmacy may retain this information for subsequent visits by the patient to the pharmacy to thereby preclude the need to re-enter some or all of it. If the pharmacy has multiple locations, the collected information may be shared between them electronically so that, if the patient goes to a different pharmacy, some or all of the information is still available.

The patient may not be able, however, to later access the collected information without physically travelling to a pharmacy. The patient may wish to edit or update the information, for example, or access other information, such as a status of a recently placed pharmacy order. In order to enable remote access (via, for example, a client computer connected to the Internet), the patient would need to present authentication information (such as a username and password) that is not part of the information collected at the pharmacy. This information might have been collected when the patient placed the pharmacy order, but doing so is inconvenient, deterring, and/or time-consuming for the patient. The patient may even already possess an online account with a store associated with the pharmacy, but without additional authentication, there is no way to link the store account with the pharmacy account with accuracy or certainty. A need therefore exists for a more convenient and simpler way for patients to authenticate to and access pharmacy account information.

SUMMARY

Embodiments of the present invention include systems and methods for authenticating a user of a store account to a pharmacy account associated with the user. In various embodiments, a user is logged into (i.e., authenticated to) and/or creates a store account via a mobile device or other client device. The client device transmits information related to a pharmacy prescription of the user, such as a prescription number, order number, pharmacy number, customer number, or the like; this information may appear on a prescription label and may be encoded thereon as a one-dimensional or two-dimensional bar code or may be any other type of identifying information, such as information from an RFID or NFC tag. The information, image, and/or information extracted from the image is transmitted to a server; the server extracts information from the image, if necessary, and may verify the validity of any labels in the image. The server then compares the information to a database of pharmacy accounts and identifies an associated patient. Based at least in part on the identified patient, the server communicates with the client to prompt the user for additional authentication information, such prescription information, location information, biometric information, answers to challenge questions, or text messages. If the additional authentication information is consistent with expected values or responses, the store account is linked to the pharmacy account, and the user may thereafter access pharmacy account information via the store account.

In a first aspect, a method for authenticating a user of a first account to a second account includes receiving, from a client device of the user, authentication information related to the first account; authenticating the user to the first account using the authentication information; receiving, from the client device of the user, electronic data comprising information related to a pharmacy prescription; electronically extracting, using the electronic data, the information related to the pharmacy prescription; identifying the second account based at least in part on the information related to the pharmacy prescription; receiving, from the client device, additional authentication information; and linking the first account to the second account if the additional authentication information is consistent with the user.

The second account may be associated with the user or a third party. A request may be transmitted to the client device for the additional authentication information based at least in part on information in the first account or second account. A type of the additional authentication information may vary based at least in part on an assessment that the user is fraudulent or erroneous in attempting to link the second account to the first. The first account may be a store account and the second account may be a pharmacy account. The information related to a pharmacy prescription may include an image of a prescription bottle label, prescription bag label, or prescription monograph, e.g., a one-dimensional or two-dimensional bar code that encodes a prescription number, order number, pharmacy number, or customer number. The additional authentication information may include prescription information, biometric information, challenge-question answers, location information, or a text message. Challenge question-and-answer pairs may be generated using information associated with the second account. A request for the additional authentication information may be transmitted to the client device and may include a request to send the text message from the client device and a sending phone number may be compared with a phone number associated with the second account. A first account database may be searched for matching accounts in a second account database and, upon finding a match, a prompt may be transmitted to the user to link the first account and second account.

In another aspect, a system for authenticating a user of a first account to a second account includes a network interface configured for communication with a client device of the user; a non-volatile computer memory for storing information associated with the first account and information associated with the second account; and a computer processor configured for executing software instructions to: receive, from a client device of the user, authentication information related to the first account; authenticate the user to the first account using the authentication information; receive, from the client device of the user, electronic data comprising information related to a pharmacy prescription; electronically extract, using the electronic data, the information related to the pharmacy prescription; identify the second account based at least in part on the information related to the pharmacy prescription; receive, from the client device, additional authentication information; and link the first account to the second account if the additional authentication information is consistent with the user.

The second account may be associated with the user or a third party. A request may be transmitted to the client device for the additional authentication information based at least in part on information in the first account or second account. A type of the additional authentication information may vary based at least in part on an assessment that the user is fraudulent or erroneous in attempting to link the second account to the first. The first account may be a store account and the second account may be a pharmacy account. The information related to a pharmacy prescription may include an image of a prescription bottle label, prescription bag label, or prescription monograph, e.g., a one-dimensional or two-dimensional bar code that encodes a prescription number, order number, pharmacy number, or customer number. The additional authentication information may include prescription information, biometric information, challenge-question answers, location information, or a text message. Challenge question-and-answer pairs may be generated using information associated with the second account. A request for the additional authentication information may be transmitted to the client device and may include a request to send the text message from the client device and a sending phone number may be compared with a phone number associated with the second account. A first account database may be searched for matching accounts in a second account database and, upon finding a match, a prompt may be transmitted to the user to link the first account and second account.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Various embodiments of the present invention include systems and methods for authenticating a user authenticated to a first user account to a second user account using received prescription information associated with the user and a follow-up authentication step. In various embodiments, with reference to FIG. 1, a computing environment 100 includes a client device 102 connected to a network 104 (such as the Internet) via a wired or wireless link. The client device 102 may be a mobile phone, smartphone, tablet computer, laptop computer, desktop computer, or similar device; in other embodiments, the client device 102 may be a point-of-sale system. The client device 102 includes or is connected to, via a network connection 106, an image-capture device 108, which may be an integrated smartphone camera, digital camera, scanner, or similar device. A store server 110 may also be connected to the network 104; the store server 110 may further be connected to or include a store account database 112 via a network or local connection 114. The computing environment may further include a pharmacy server 116, which may be connected to or include a pharmacy account database 118 via a network or local connection 120. The pharmacy server 116 may be in communication with the client device 102 and/or store server 110 via the network 104; in other embodiments, the pharmacy server 116 is in communication with the store server 110 via a separate, private network.

Figure 1:
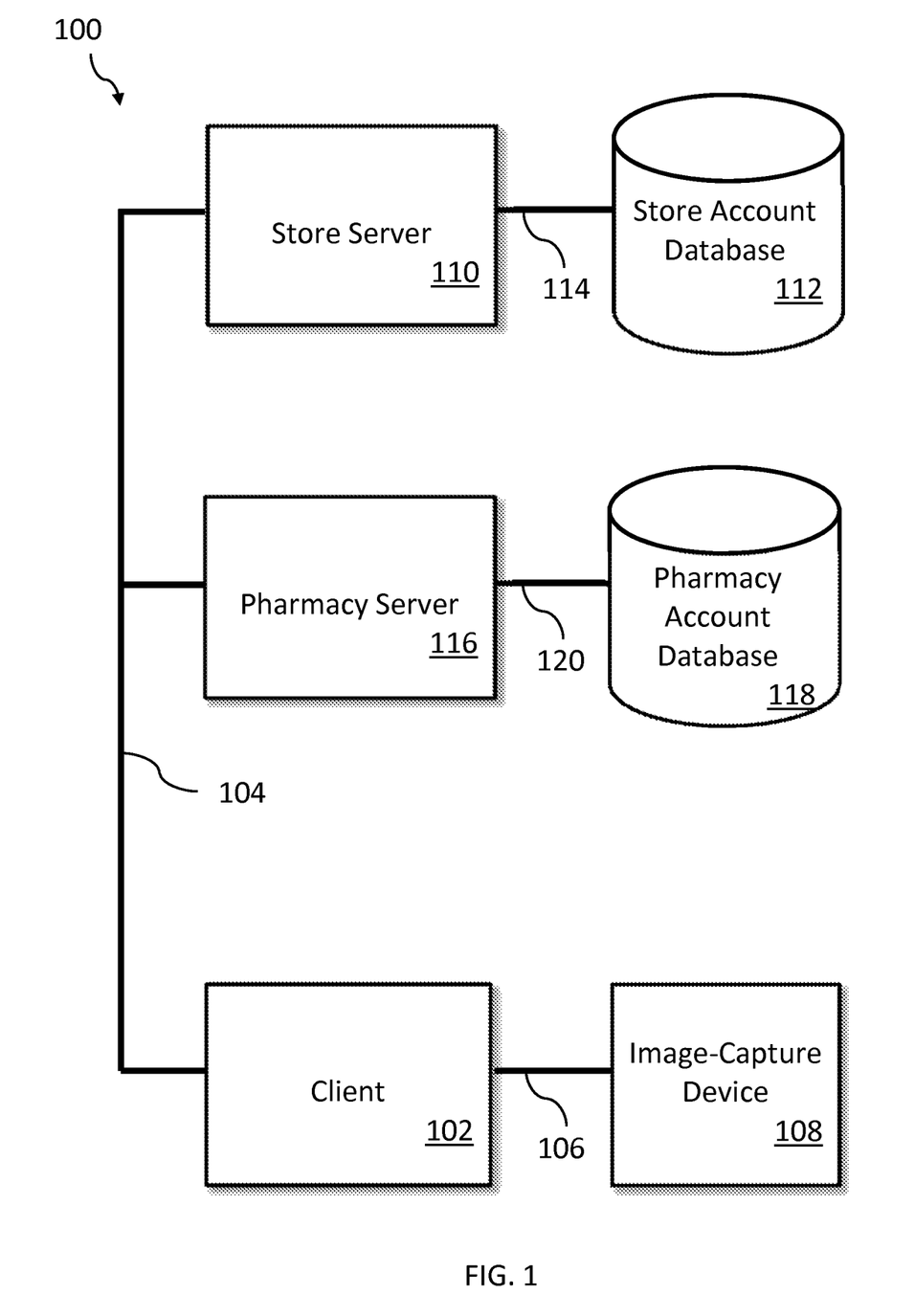
FIG. 1 illustrates a system for authenticating a user of a first user account to a second user account in accordance with an embodiment of the present invention.

One of skill in the art will understand that the disclosed embodiments of the present invention are not limited to only the configuration of the environment 100, however, and that other configurations of the servers 110, 116 and client device 102 are within the scope of the present invention. For example, any number of servers 110, 116 and clients 102 may be used; in some embodiments, some or all of the functionality of the servers 110, 116 may be implemented on a single server 110, 116 and/or on the client 102.

Figure 2:
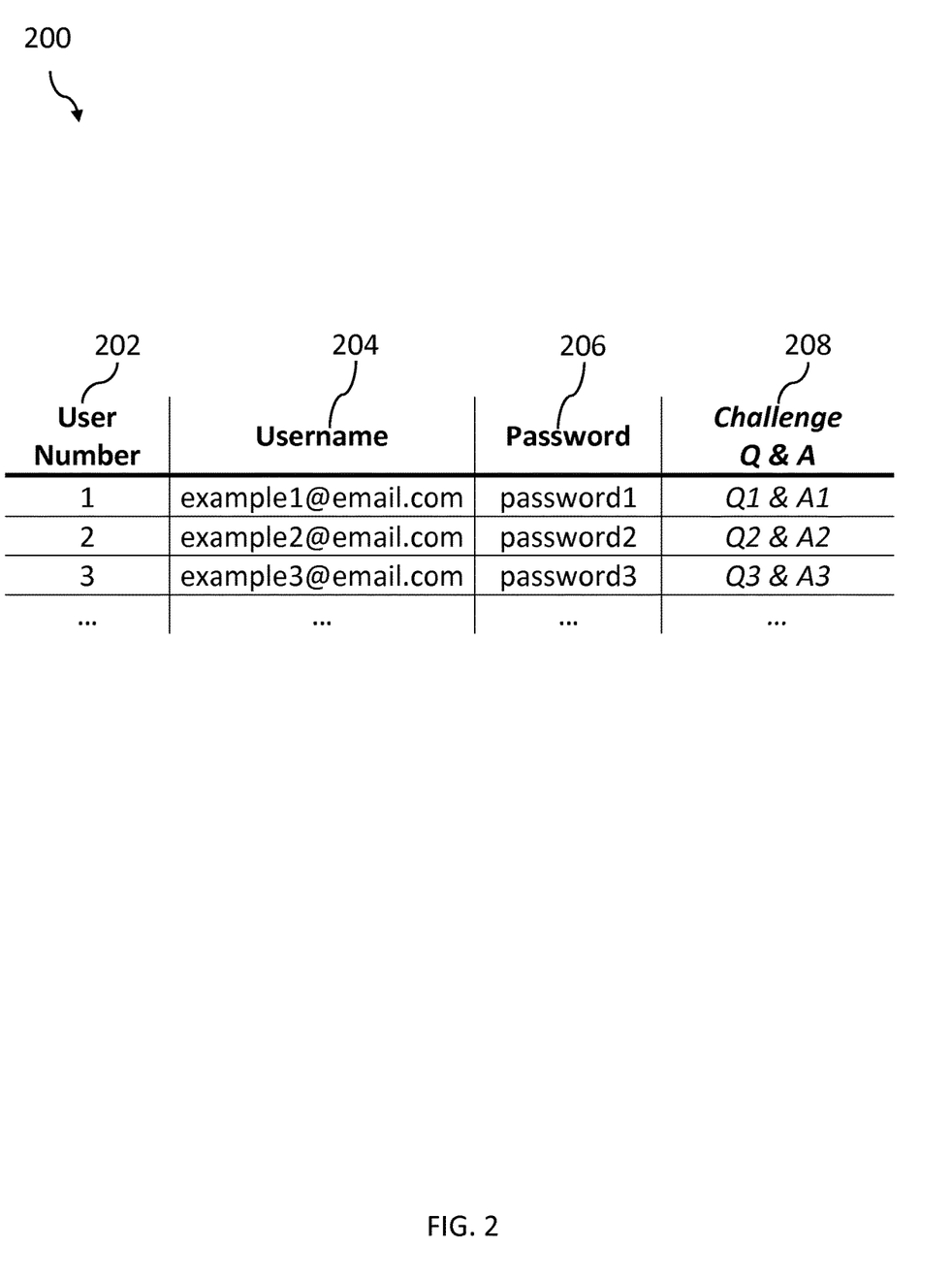
FIG. 2 illustrates an exemplary first user-account database in accordance with an embodiment of the present invention.

FIG. 2 illustrates a plurality of exemplary entries 200 in the store account database 112; the present invention, however, is not limited to any particular type, format, or arrangement of entries. The entries 200 may include, for each store account, a user number 202, a username 204 (which may be an email address of the user or any other username), and a password 206 (which may be stored using encryption, salting, or any other type of password protection system). In some embodiments, the entries 200 further include a pre-selected challenge question and answer 208. Any other type of user information, as mentioned above, may be associated with each entry 200. In some embodiments, the user's store account includes further user information, such as the user's name, address, phone number, email address (if different from the username), payment information (such as credit-card information), shopping cart, wishlist, order history, coupons, gift certificates, or any other similar information. Entries 200 in the store account database 112 may be pre-existing or may be created before, during, or after the linking of the store account to the pharmacy account, as described herein.

Figure 3:
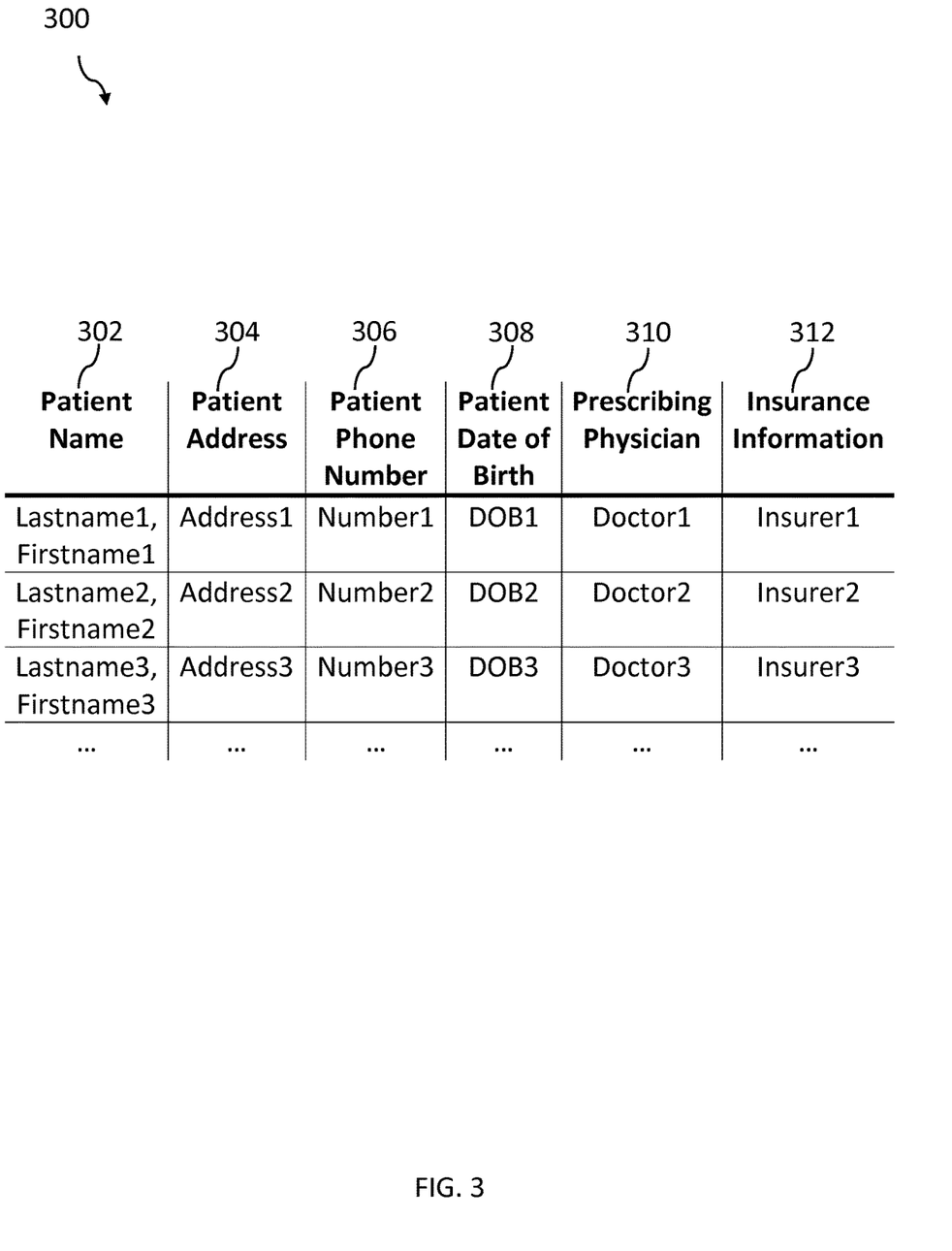
FIG. 3 illustrates an exemplary second user-account database in accordance with an embodiment of the present invention.

FIG. 3 illustrates a plurality of exemplary entries 300 in the pharmacy account database 118; the present invention, however, is not limited to any particular type, format, or arrangement of entries. The entries 300 may include, for each pharmacy account, a patient name 302, a patient address 304, a patient phone number 306, a patient date of birth 308, a prescribing physician 310, and/or insurance information 312. Any other type of patient information may be associated with each entry 300.

Figure 4:
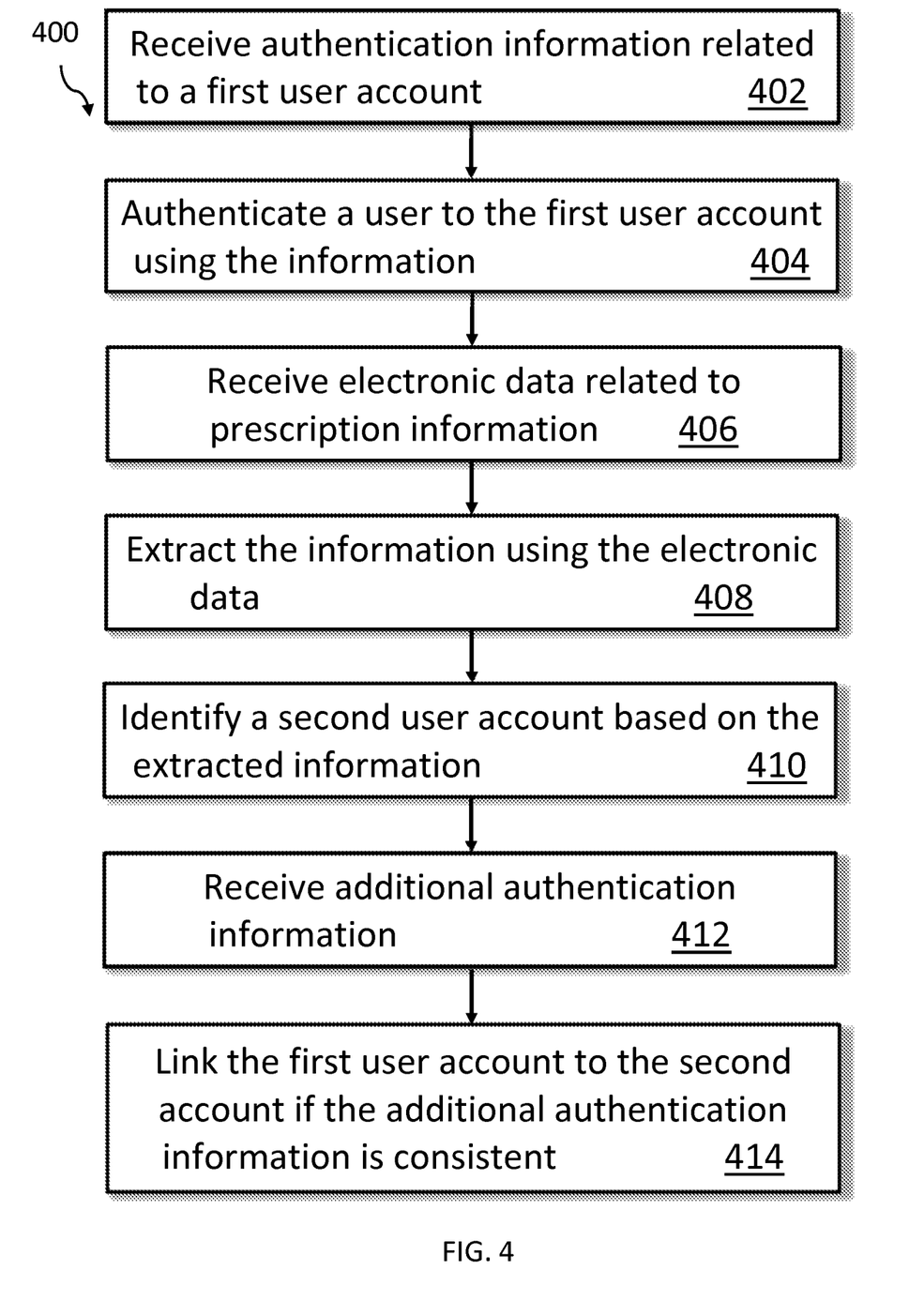
FIG. 4 illustrates a method for authenticating a user of a first user account to a second user account in accordance with an embodiment of the present invention.

FIG. 4 illustrates a method 400 for authenticating a user of a first user account (e.g., a store account) to a second user account (e.g., a pharmacy account). Authentication information related to the first user account associated with the user is received (402); the user is authenticated (404) to the first account using the authentication information. This authentication may include accessing an existing account or creating a new account. Electronic data, such as an electronic image, data from an RFID or NFC tag, or any other type of electronic information, that includes information related to a pharmacy prescription is received (406). The information is extracted (408) using the data, and the second account is identified (410) based on the extracted information. The information may be extracted directly from the electronic data if the information is contained therein, such as if the electronic data is a photograph of a prescription label. Alternatively or in addition, the information may be extracted using the electronic data as a key or index into a database of information, such as if the electronic data is information received from an RFIC or NFC tag, and this information is used to look up the prescription information in a database. Additional authentication information is received (412) from the client device; in some embodiments, in response to a prompt for the additional information based at least in part on information in the second account. The first and second accounts are linked (414) if the additional authentication information is consistent with the user.

In the first step 402, the store server 110 receives authentication information related to the store account via the network 104. In some embodiments, the client device 102 executes a native or thin-client application (e.g., a web browser) that allows the user to log in and access store-server functions, such as online shopping. The user of the client device 102 enters authentication information into the client device 102 via a user-input device in electronic communication with the client 102, such as a keyboard, touchscreen, mouse, microphone, fingerprint reader, biometric scanner, or other such device. The authentication information may include a username, password, voice command or input, fingerprint, heart-rate pattern, or other similar input. In some embodiments, the client device 102 transmits some or all of the authentication information to the store server 110 over the network 104; the authentication information may be encrypted or otherwise protected prior to transmission. The authentication may be received from a user having an existing account or from a user setting up a new account.

In the second step 404, the user is authenticated to the first account using the received authentication information. Any system or method of authentication known in the art is within the scope of the present invention. In some embodiments, the received username is used as an index into a database of username/password tuples, and a stored password is retrieved based thereon; the stored password is thereafter compared to the received password. The stored password may be stored in an encoded, encrypted, and/or salted form; the receive password may first be similarly encoded, encrypted, and/or salted before the comparison. If the user is setting up a new account, the received password is stored in the database as the new stored password. In other embodiments, the user's name, location, phone number, address, or other such information and/or the client device's network address, machine access code, or other such attribute is used in place of or in addition to the username. Similarly, facial recognition, biometric information, fingerprints, or other such information may be used in place of or in addition to the password.

The authentication may be performed by the store server 110 and/or the client 102. For example, the client 102 may transmit a request for the stored password to the store server 110 and receive the stored password back in response; the client 102 may thereafter compare the received password with the stored password. Any division of the authentication process between the client 102 and the store server 110 is within the scope of the present invention.

Once authenticated, the store server 110 and/or pharmacy server 116 may search the pharmacy account database 118 for entries matching the authenticated entry in the store account database. The search may include matching or similar usernames, email addresses, passwords, or any other information available in each database 112, 118 (such as, for example, names, addresses, social security numbers, prescription information, or any other information). If matching information is found, the store server 110 and/or pharmacy server 116 may transmit a prompt to the user of the client device 102 to link the store and pharmacy accounts, as explained below. In some embodiments, if an exact match is found, the store server 110 and/or pharmacy server 116 creates the link automatically and optionally transmits a message to the user of the client device 102 notifying of the creation of the link.

Once authenticated, the client 102 may retain a key, token, cookie, or similar indication of successful authentication in a local memory or other storage; subsequent requests by the user to access the store database 112 may thus not require re-transmission of the authentication information. The user may remain authenticated to the client 102 indefinitely, until a certain amount of time (e.g., one day) has elapsed, until the user logs out of an application on the client 102, until the user powers down the client 102, or any similar event or amount of time. In some embodiments, the first two steps 402, 404 are performed immediately prior to the remainder of the steps 406-414, such as when, for example, the user wishes to link the pharmacy account to the store account but is not already authenticated to the store account. In other embodiments, the user has authenticated to the store account prior to the attempt to link the two accounts. In other words, the second step 404 and the third step 406 may be separated in time by any amount of time. In still other embodiments, the first steps 402, 404 are performed during or after the later steps 406-414 if, for example, the user has not yet created a store account—creation of the store account may occur after, for example, the electronic image is received.

In the third step 406, an electronic image that includes prescription information is received by the store server 110. In some embodiments, the electronic image is an image of a prescription label, such as a label affixed to a pill bottle, pharmacy shopping bag, or other medication container. The client 102 and/or store server 110 may, in a fourth step 408, extract information from the image of the prescription label using, for example, optical-character recognition, edge detection, pattern matching, or any other technique known in the art. The information may include a prescription number, order number, pharmacy number, and/or customer number. The information may be printed on the label using alpha-numeric characters, encoded in one- or two-dimensional barcodes, or appear in any other format or encoding.

In some embodiments, the client 102 and/or store server 110 verifies that any numbers extracted from the image are correct. For example, the client 102 and/or store server 110 may compare an extracted number to a list or database of known good numbers to verify that the number is in an expected format. For example, the number originally encoded in a barcode may begin with a fixed start sequence of digits, such as "28"; if the first two digits of the extracted number do not match this start sequence, the server 110 and/or client 102 may halt the process and/or ask the user to re-scan the barcode. Similarly, another sequence of digits in the number may correspond to a prescription number, prescription refill number, edit version number, partial fill sequence number, store number indicator, or store number; if, for example, the store number (or any other number) does not reflect an expected or existing store number (or any other number), the server 110 and/or client 102 may also or in addition halt the process and/or ask the user to re-scan the barcode. If more than two numbers are extracted, the server 110 and/or client 102 may verify that they belong to or are otherwise associated with the same user or patient.

A software application executing on the client 102 may guide the user in taking or scanning the image. The client application may prompt the user to capture the image with a user interface that includes visual guides, such as a crosshair, image-boundary rectangle, or other such features. Once captured, the client 102 and/or store server 110 may test the quality of the image by, for example, measuring a light level or blurriness level of the image. If the image is inadequate, the client 102 may prompt the user to capture another image of the card or document. The client application may be a standalone application for linking and thereafter accessing the pharmacy server 116; in other embodiments, the client application is a store-server access application that includes other features, such as online shopping. The client application may be a client-native application, web-browser application, or any other type of application.

In a fifth step 410, a second account (e.g., a pharmacy account) is identified based on the extracted information. In some embodiments, the store server 110 transmits a query to the pharmacy server 116 that includes some or all of the extracted information. In some embodiments, the pharmacy server 116 searches the pharmacy account database 118 for the user's pharmacy account. For example, the store server 110 and/or pharmacy server 116 may search the entries in the pharmacy account database 118 for an entry that matches some or all of the information extracted from the image. For example, the pharmacy server 116 may query the pharmacy account database 118 with the order number, prescription number, and/or customer number and thereby identify an entry associated with one or all numbers. In some embodiments, the second account is associated with a person other than the user, such as a family member or trusted third party. This other person may have granted permission to the user to access his or her pharmacy account by previously configuring his or her pharmacy account to indicate the identity of the user and/or grant of permission. For example, the user and/or other person may have linked their pharmacy accounts by indicating that they are family members. In other embodiments, the user does not possess a pharmacy account; in these embodiments, the other person may specify additional authentication information to his or her pharmacy account, and this additional authentication information is used to authenticate the user.

If a match is found in the pharmacy account database 118, the pharmacy server 116 may transmit information associated with the matching entry to the store server 110, such as a patient identity, patient identification number, prescription information (such as a medication name, medication dosage, prescribing physician's name), or other patient information (such as date of birth, gender, or prescription history).

The store server 110 transmits a message to the client 102 that prompts the user, via a user interface of the client 102, to enter additional authentication information. In some embodiments, the request for information is based at least in part on the received patient information and/or information in the store account database 112. The request for the additional authentication may include, for example, a request for additional prescription information, location information, biometric information, security challenge-question answers, or text messages. After the user enters the information, it is transmitted from the client 102 and, in a sixth step 412, received at the store server 110.

The one or more types of authentication information requested and received may be selected to be the same for all users attempting to link a store account to a server account by, for example, a system administrator for the store server 110 and/or pharmacy server 116. In other embodiments, a plurality of types of authentication information is presented to the user via a display of the client device 102, and the user selects a preferred type or types of authentication information. The plurality of types presented to the user may be all types supported by the store server 110 or a subset of all supported types.

In some embodiments, the store server 110 selects a type or types of additional authentication information based on information stored in the store database 112 and/or pharmacy database 118. If, for example, the stored information indicates that the attempt to link the store account to the pharmacy account is less likely to be fraudulent or erroneous, the store server 110 may select a more convenient but less secure type of additional authentication information, such as location information (which may be gathered from the client device 102 without interaction from the user). The store server 110 may determine that the attempt is less likely to be fraudulent or erroneous if, for example, the location of the client device 102 matches that of a pharmacy frequented by the patient in the matching entry in the patient account database 118; if the type of medication captured in the prescription-information image is not high-risk; if no previous, unsuccessful attempts to link the store account to the pharmacy account have been made; if an email address associated with the store account is not a known fraudulent address (i.e., it does not appear in the store-account database 118 or other third-party database as a spam email); if the password associated with the store account is relatively strong and secure (i.e., it does not contain a dictionary word or common password string); and/or any other such factor. If one or more of these factors are not true, the store server 110 may determine that the attempt to link the accounts is more likely to be fraudulent or erroneous and may therefore require a less convenient but more secure type of additional authentication information, such as, for example, a security question and answer, biometric information collected by the client 102, and/or a text message sent from a phone number listed in the entry in the pharmacy account database. The security question and answer may be selected in advance by the patient and stored in the pharmacy account database 118 or may be generated in real time by searching for public Internet information available about the user. Alternatively or in addition, the security question and answer may be based on information present in the entry in the pharmacy account database 118, such as the patient's address, telephone number, and/or credit card number.

If the additional authentication information is consistent (i.e., it matches expected values), the store server 110 and/or pharmacy server 116 creates a link between the two accounts, thereby permitting the user to access some or all of the linked entry in the pharmacy account database 118 via the store server 110 if and when the user is authenticated to the store server 110. If the additional authentication is not consistent, the store server 110 and/or pharmacy server 116 may send a request to the client 102 for further authentication information and/or a request for the user to resolve or explain any discrepancies. The request may further or instead include a prompt for the user to contact a technician via phone, fax, email, or other means to resolve any discrepancies.

Figure 5:
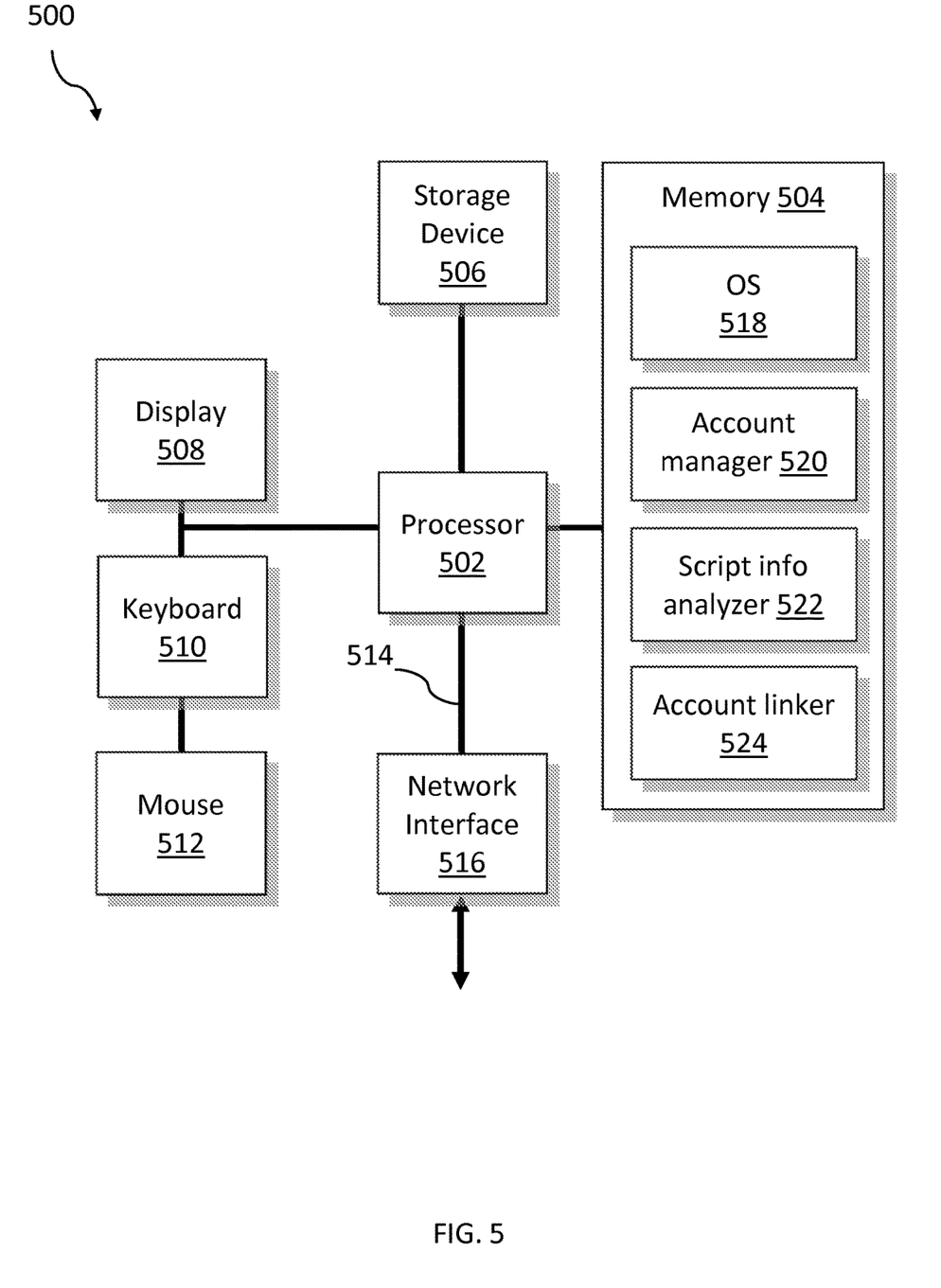
FIG. 5 illustrates an exemplary server computing device in accordance with an embodiment of the present invention.

FIG. 5 is a simplified block diagram of a suitably programmed general-purpose server 500 implementing embodiments of the present invention; the server may be the store server 110, pharmacy server 116, or host part of either or both servers 110, 116. The server 500 includes a processor 502 having one or more central processing units (CPUs), volatile and/or non-volatile main memory 504 (e.g., RAM, ROM, or flash memory), one or more mass storage devices 506 (e.g., hard disks, or removable media such as CDs, DVDs, USB flash drives, etc. and associated media drivers, which may be used for the store account database 112 and/or pharmacy account database 118), a display device 508 (e.g., a liquid-crystal display (LCD) monitor), user-input devices such as a keyboard 510 and a mouse 512, and one or more buses 514 (e.g., a single system bus shared between all components, or separate memory and peripheral buses) that facilitate communication between these components. A network interface 516 (e.g., a Wi-Fi or ETHERNET port) may be used to connect the computer 500 to the Internet or other network.

The main memory 504 may be used to store instructions to be executed by the processor 502, conceptually illustrated as a group of modules. These modules generally include an operating system 518 (e.g., a Microsoft WINDOWS, Linux, or APPLE OS X operating system) that directs the execution of low-level, basic system functions (such as memory allocation, file management, and the operation of mass storage devices), as well as higher-level software applications, such as a store and/or pharmacy account manager 520 (for, e.g., authenticating a user to a store account, creating a new store account, or allowing access to a pharmacy account via a store account), a prescription information analyzer 522 (for, e.g., extracting information from images), and an account linker 522 (for, e.g., linking a store account to a pharmacy account). The various modules may be programmed in any suitable programming language, including, without limitation high-level languages such as C, C++, Java, Perl, Python, or Ruby or low-level assembly languages. The memory 504 may further store input and/or output data associated with execution of the instructions as well as additional information used by the various software applications.

Figure 6:
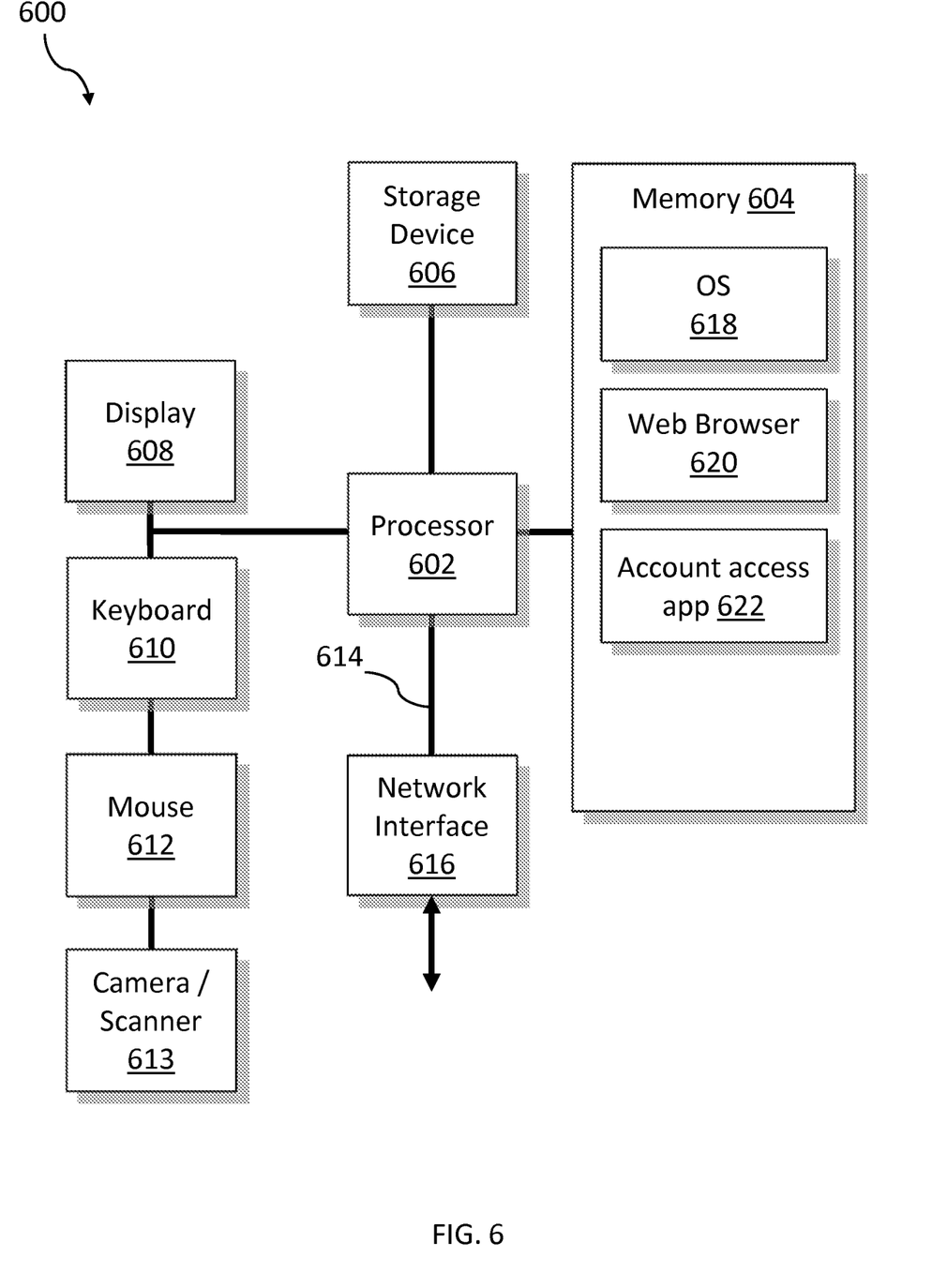
FIG. 6 illustrates an exemplary client computing device in accordance with an embodiment of the present invention.

FIG. 6 is a simplified block diagram of a suitably programmed client device 600 for capturing information from a user and displaying an order status thereto. Like the server 500, the client device 600 includes a processor 602, a memory 604, a storage device 606, a display 608, a keyboard 610, a mouse 612, buses 614, and a network interface 616. The client 600 may further include a camera/scanner 613 for capturing images. The client 600 and the server 500 may communicate via a network such as the Internet using the network interfaces 516, 616. The user input and output interfaces described herein may be presented to the user via a web browser 620 and/or a client-native application 622.

The server 500 and client 600 are described herein with reference to particular blocks, but this description is not intended to limit the invention to a particular physical arrangement of distinct component parts. The computers 500, 600 are illustrative examples; variations and modifications are possible. Computers 500, 600 may be implemented in a variety of form factors, including server systems, desktop systems, laptop systems, tablets, smartphones or personal digital assistants, and so on. A particular implementation may include other functionality not described herein, e.g., wired and/or wireless network interfaces, media playing and/or recording capability, etc. In some embodiments, one or more cameras may be built into the computer rather than being supplied as separate components. Further, the computer processor may be a general-purpose microprocessor, but depending on implementation can alternatively be, e.g., a microcontroller, peripheral integrated circuit element, a customer-specific integrated circuit ("CSIC"), an application-specific integrated circuit ("ASIC"), a logic circuit, a digital signal processor ("DSP"), a programmable logic device such as a field-programmable gate array ("FPGA"), a programmable logic device ("PLD"), a programmable logic array ("PLA"), smart chip, or other device or arrangement of devices.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method for authenticating a first user of a first account to a second account, the method comprising:
receiving at a store server over a communication network authentication information from a client device of a first user related to the first account of the first user;
authenticating at the store server the first user to the first account using the authentication information and information stored in a first account database;
electronically capturing electronic data from a prescription bottle label using a camera associated with the client device, wherein the electronic data includes information related to a pharmacy prescription, and wherein at least an encoded portion of the electronic data is electronically encoded in a format known to the store server;
responsive to authenticating the first user, receiving at the store server over the communication network the electronic data captured by the client device from the prescription bottle label and comprising the information related to the pharmacy prescription;
electronically extracting by the store server electronic information from the electronic data and electronically decoding the encoded portion, wherein the extracted information is related to the pharmacy prescription;

verifying by the store server that the extracted information related to the pharmacy prescription is valid and is associated with a particular user;

determining that the particular user associated with the information related to the pharmacy prescription is a second user;

identifying the second account associated with the second user in the pharmacy database by searching a second account database for an entry matching the extracted information related to the pharmacy prescription;

receiving, from the client device of the first user, additional authentication information including location information of the client device of the first user without interacting with the first user;

automatically creating a link between the first account of the first user in the store database and the second account of the second user in the pharmacy database based at least in part on the electronic data captured from the prescription bottle label if the additional authentication information is consistent with an expected value, wherein the link provides a permission for the first user authenticated to the first account associated with the first account database to remotely access one or more entries in the second account database associated to the second account from the client device of the first user;

responsive to creating the link between the first account of the first user in the store database and the second account of the second user in the pharmacy database, generating and transmitting a message for the first user to notify the creation of the link and to access the entries of the second account database; and the first user accessing the second account of the second user in the pharmacy database based at least in part on the link determined using the electronic data captured from the prescription pill bottle label.

2. The method of claim 1, wherein the second user is a family member of the first user or a trusted third party.

3. The method of claim 1, further comprising transmitting, to the client device, a request for the additional authentication information based at least in part on information in the first account or the second account.

4. The method of claim 3, wherein a type of the additional authentication information varies based at least in part on an assessment that the first user is fraudulent or erroneous in attempting to create the link between the second account and the first account.

5. The method of claim 1, wherein the first account comprises a store account and the second account comprises a pharmacy account.

6. The method of claim 1, wherein the electronic data comprising the information related to the pharmacy prescription comprises an image of a prescription bottle label, a prescription bag label, or a prescription monograph.

7. The method of claim 6, wherein the image comprises a one-dimensional or two-dimensional bar code that encodes a prescription number, an order number, a pharmacy number, or a customer number.

8. The method of claim 1, wherein the additional authentication information comprises prescription information, biometric information, challenge-question answers, or a text message.

9. The method of claim 8, further comprising generating challenge question-and-answer pairs using information associated with the second account.

10. The method of claim 8, further comprising transmitting, to the client device, a request for the additional authentication information by requesting the client device to send a text message and comparing a sending phone number related to the text message with a phone number associated with the second account.

11. The method of claim 1, further comprising searching the first account database for matching accounts in the second account database and, upon finding a match, transmitting a prompt to the first user to create the link between the first account and the second account.

12. A system for authenticating a first user of a first account to a second account, the system comprising:
a network interface configured for communication with a client device of the first user;
a non-volatile computer memory for storing information associated with the first account and information associated with the second account; and
a computer processor configured for executing software instructions to:
receiving at a store server over a communication network authentication information from a client device of a first user related to the first account of the first user;
authenticate at the store server the first user to the first account using the authentication information and information stored in a first account database;
responsive to authenticating the first user, receive at the store server over the communication network the electronic data captured by the client device from the prescription bottle label and comprising the information related to the pharmacy prescription;
electronically extract by the store server electronic information from the electronic data and electronically decode the encoded portion, wherein the extracted information is related to the pharmacy prescription;
verify by the store server that the extracted information related to the pharmacy prescription is valid and is associated with a particular user;
determine that the particular user associated with the information related to the pharmacy prescription is a second user;
identify the second account associated with the second user in the pharmacy database by searching a second account database for an entry matching the extracted information related to the pharmacy prescription;
receive, from the client device of the first user, additional authentication information including location information of the client device of the first user without interacting with the first user;
automatically create a link between the first account of the first user in the store database and the second account of the second user in the pharmacy database based at least in part on the electronic data captured from the prescription bottle label if the additional authentication information is consistent with an expected value, wherein the link provides a permission for the first user authenticated to the first account associated with the first account database to remotely access one or more entries in the second account database associated to the second account from the client device of the first user; and
responsive to creating the link between the first account of the first user in the store database and the second account of the second user in the pharmacy database, generate and transmit a message for the first user to notify the creation of the link and to access the entries of the second account database the first user;

the first user to access the second account of the second user in the pharmacy database based at least in part on the link determined using the electronic data captured from the prescription pill bottle label; and a camera operably coupled to the computer processor and configured to:

electronically capture the electronic data from the prescription bottle label using the camera associated with the client device, wherein the electronic data includes information related to the pharmacy prescription, and wherein at least an encoded portion of the electronic data is electronically encoded in a format known to the store server.

13. The system of claim 12, wherein the second user is a family member of the first user or a trusted third party.

14. The system of claim 12, wherein the computer processor is further configured to execute software instructions to transmit, to the client device, a request for the additional authentication information based at least in part on the information associated with the first account or the second account.

15. The system of claim 14, wherein a type of the additional authentication information varies based at least in part on an assessment that the first user is fraudulent or erroneous in attempting to create the link between the second account to the first account.

16. The system of claim 12, wherein the first account comprises a store account and the second account comprises a pharmacy account.

17. The system of claim 12, wherein the electronic data comprising the information related to the pharmacy prescription comprises an image of a prescription bottle label, a prescription bag label, or a prescription monograph.

18. The system of claim 17, wherein the image comprises a one-dimensional or two-dimensional bar code that encodes a prescription number, an order number, a pharmacy number, or a customer number.

19. The system of claim 12, wherein the additional authentication information comprises prescription information, biometric information, challenge-question answers, or a text message.

20. The system of claim 12, wherein the computer processor is further configured to execute software instructions to search the first account database for matching accounts in the second account database and, upon finding a match, transmit a prompt to the first user to create the link between the first account and the second account.

\* \* \* \* \*